United States Patent
Bilof et al.

[19]

[11] Patent Number: 5,918,739
[45] Date of Patent: Jul. 6, 1999

[54] FULL LEVEL INDICATOR FOR MEDICAL DISPOSABLES CONTAINER

[76] Inventors: Richard M. Bilof, 7017 Miller Rd., Wonder Lake, Ill. 60097; James R. Wingfield, 563 Cress Creek La., Crystal Lake, Ill. 60014

[21] Appl. No.: 09/083,655

[22] Filed: May 23, 1998

[51] Int. Cl.$^6$ .................................................. B65D 83/10
[52] U.S. Cl. ...................... 206/366; 206/370; 206/459.1
[58] Field of Search .................................... 206/364, 365, 206/366, 370, 459.1; 604/110, 111, 192

[56] References Cited

U.S. PATENT DOCUMENTS

| | | | |
|---|---|---|---|
| 4,519,306 | 5/1985 | LaBarge | 100/35 |
| 4,573,984 | 3/1986 | Benzies | 604/339 |
| 5,351,381 | 10/1994 | Case | 29/283.5 |
| 5,482,207 | 1/1996 | Nelson et al. | 232/43.2 |
| 5,508,681 | 4/1996 | Nelson et al. | 340/540 |
| 5,791,471 | 8/1998 | Radmand | 206/366 |

*Primary Examiner*—David T. Fidel
*Attorney, Agent, or Firm*—Michael Best & Friedrich LLP

[57] ABSTRACT

A sharps disposal container comprising a container including a cover having an opening formed therein for receiving sharps. An emitter and detector are mounted on the container with the emitter being oriented for projecting a beam toward the container. Reflectors are positioned in the container for receiving the beam from the emitter, projecting the beam across the container and from side to side at a predetermined level and for projecting the beam to the detector. An indicator or alarm is connected to the detector for providing an indication when the level of sharps in the container is sufficient to interrupt the beam. The indicator may include a counter for counting the number of sharps placed in the container.

16 Claims, 4 Drawing Sheets

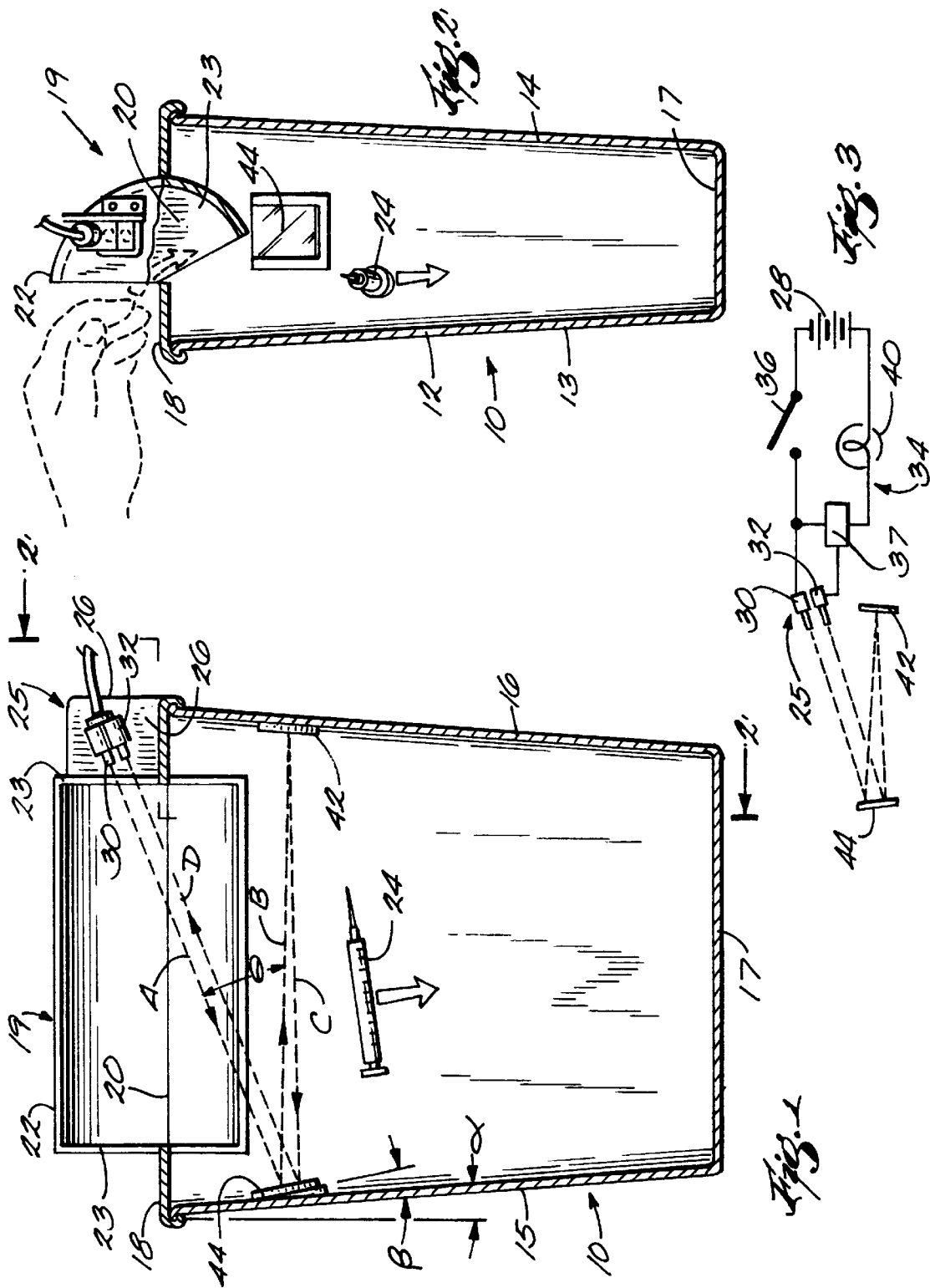

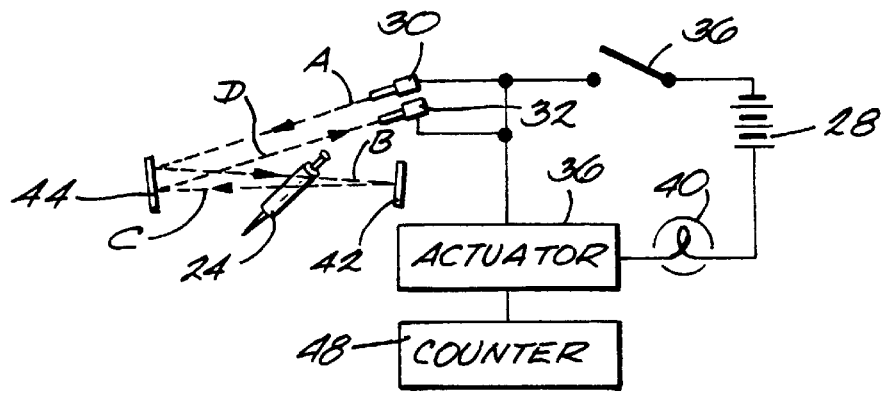
Fig. 4
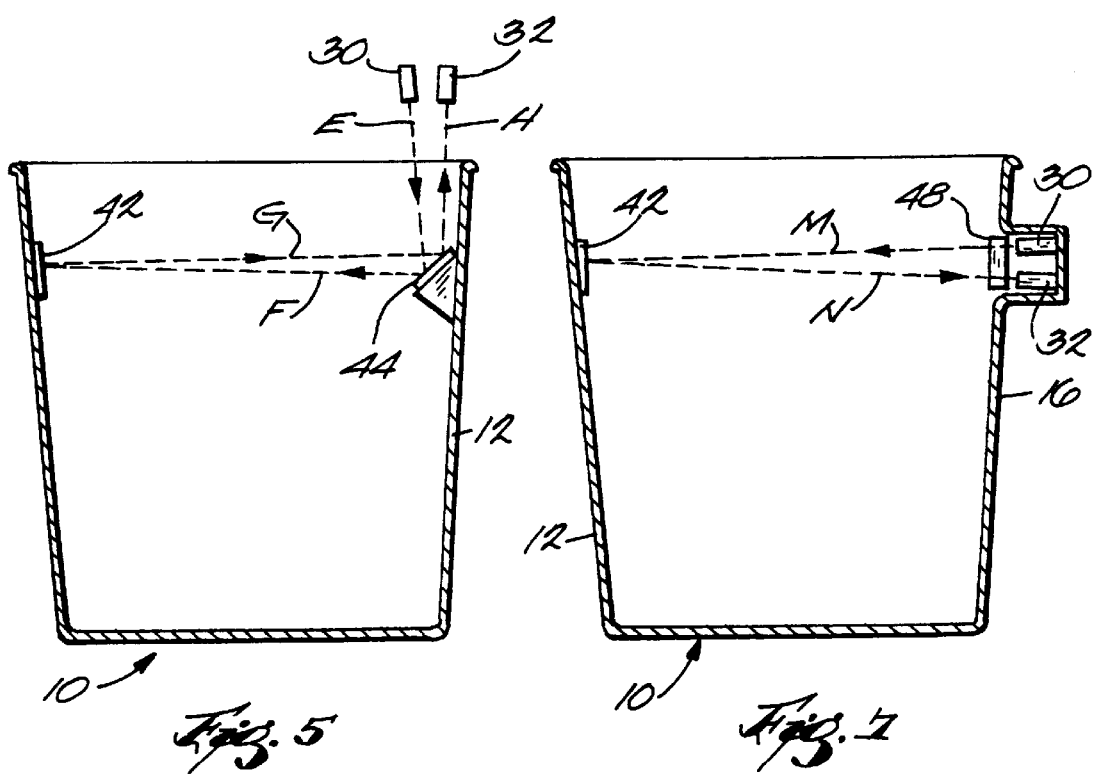
Fig. 5
Fig. 7

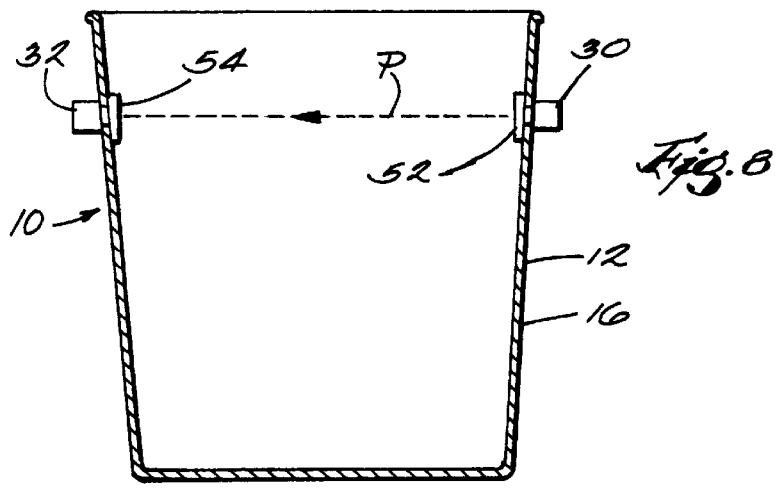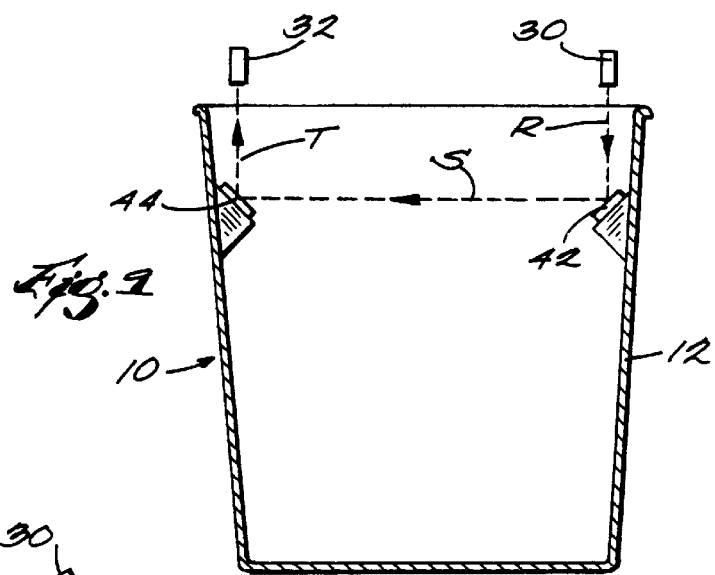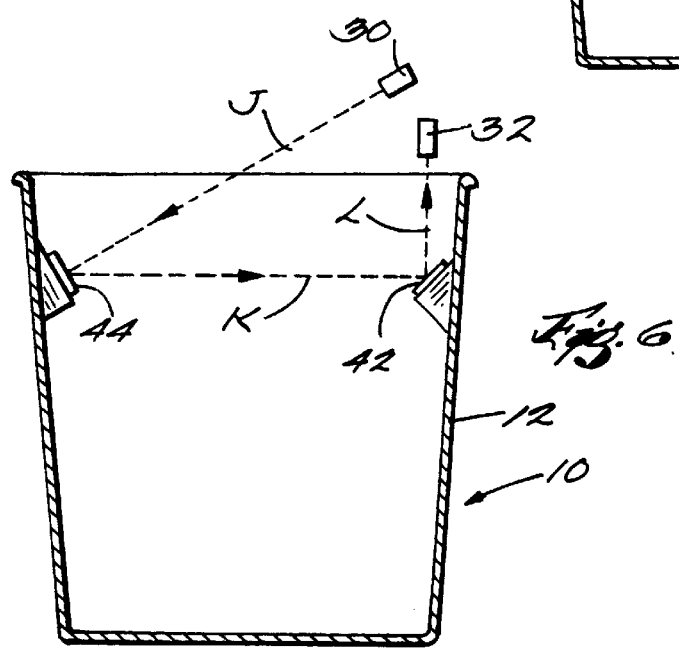

FULL LEVEL INDICATOR FOR MEDICAL DISPOSABLES CONTAINER

BACKGROUND ON THE INVENTION

This invention relates to container level indicators and more particularly to level indicators for disposable medical sharps containers.

Diagnostic and therapeutic medical procedures routinely involve the need to penetrate the patient's tissues with a sharp needle, syringe or lancet, commonly called sharps, through which medicines are injected and/or specimens are withdrawn or extracted for analysis. This practice has the potential to expose medical personnel to various biological hazards. The primary hazard and an important component of the risk associated with this procedure is an unintended secondary stick. This problem has been well documented by health care professionals.

While there are factors which are not entirely under the control of the health care provider, such as an agitated patient, secondary sticks are most often the result of lapses of procedural control. The opportunity for mishandling to occur is increased the longer the sharp needle, or lancet point is exposed. For this reason, a sharps disposable container (SDC) has become an important element in a safety strategy which seeks to minimize the exposure time by proximate location and protecting personnel from needle sticks during subsequent handling.

SDCs have evolved to their present form as a result of certain design considerations. These included: unimpeded access for the largest syringes and needles; sufficient size to accommodate a sufficient volume of material to avoid frequent replacement; and visibility of the contents of the container to permit an assessment of their level. Because of different emphasis of these use factor requirements in the hospital setting, there is no single design which is generally accepted as best for all circumstances of use.

If the use of sharps are confined to areas frequented only by medical personnel, the design objectives for SDC's would be easier to define. However, examining rooms, wards and outpatient facilities are areas which medical personnel must share with the general public. For example, visibility of contents is sometimes distracting to patients and an invitation to the curiosity or malicious intent of the visitor. The disposal advantage becomes a disadvantage under these conditions. There are circumstances, therefor, for which the contents of an SDC should not be casually visible and access restricted. However, restricting access does not discriminate between medical and nonmedical personnel and can make the disposal task more difficult.

SUMMARY OF THE INVENTION

It is an object of the invention to provide a new and improved level indicator for medical sharps disposal containers.

Another object of the invention is to provide a medical sharps disposal container which permits easy access but minimizes the risk of a secondary needle stick as a result of overfilling the container.

A further object of the invention is to provide a disposal container for medical sharps which restricts casual visibility but permits a determination of when the contents in the container reach a level commensurate with safe handling.

It is yet another object of the invention to provide a level indicator which continuously monitors the level of sharps in an SDC container.

It is a still further object of the invention to provide an indicator which determines the number of sharps deposited in an SDC container.

These and other objects and advantages of the present invention will become more apparent from the detailed description thereof.

In general terms, the invention comprises a sharps disposal container including a container having an interior and a cover. An opening is formed in the cover to permit sharps to be inserted into the interior of the container. An emitter and a detector are mounted on the container, the emitter being oriented for projecting a beam toward the container. Reflector means are positioned in the container for reflecting the beam across the container at a predetermined level and to the detector. An indicator is coupled to the detector. The detector is operative to actuate the indicator when the level of sharps in the container reaches the predetermined level to interrupt the beam. According to a more specific aspect of the invention, the detector actuates an indicator each time an object passes through the beam.

According to a still more specific aspect of the invention, the container has a pair of opposite sides, the emitter and detector being positioned above the cover and adjacent one side of the container. The emitter is oriented to project a beam toward the second side of the container and the reflector means comprises a first reflector on the second side of the container for receiving the beam from the emitter and oriented to reflect the beam across the container at the predetermined level and toward the one side of the container. A second reflector is mounted on the one side of the container for redirecting the beam whereby the beam is reflected to the detector. According to a still more specific aspect of the invention, the second reflector is oriented for reflecting the beam across the container and to the first reflector and the first reflector is oriented for projecting the beam to the detector.

BRIEF DESCRIPTION OF THE INVENTION

FIG. 1 is a side sectional view of a level indicator for a sharps disposal container according to the invention;

FIG. 2 is a view taken along lines to 2—2 of FIG. 1;

Figure 10:
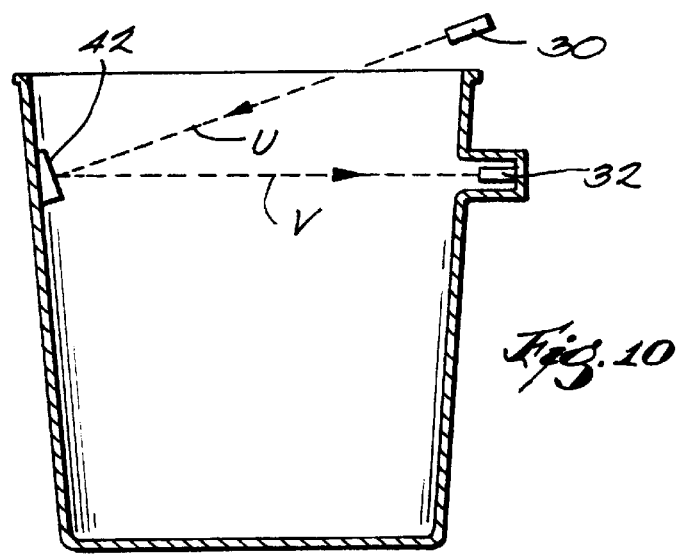

FIG. 3 schematically illustrates the level indicator of FIG. 1;

FIG. 4 shows an alternate embodiment of the level indicator;

FIGS. 5–11 show further embodiments of the invention.

DETAILED DESCRIPTION OF THE PREFERRED EMBODIMENT

FIGS. 1 and 2 illustrate a sharps disposal container (SDC) 10 consisting of a basket 12 formed of any suitable material, such as polyvinyl chloride, which is disposable and sufficiently strong and thick to resist puncture by syringes, needles and lancets and the like, commonly called sharps. The basket 12 includes opposed sidewalls 13 and 14, end walls 15 and 16 and a bottom 17. The upper end of the basket 12 is closed by a fixed cover 18 which is preferably of a material similar to basket 12 but which is also transparent to light of certain frequency ranges, particularly infrared radiation. A chute 19 is fixed in an opening 20 formed in the cover 18 and adjacent one side of basket 12. The chute 18 includes a sidewall 22 which is arcuate in transverse cross-section and a pair of end walls 23. This permits disposables, such as syringes 24, to be inserted into the basket 12 but impedes the intrusion of an individual's hand into the basket 12.

However, it is still possible for an individual to insert his fingers to some extent. Therefore, it is desirable to maintain a buffer zone between the sharps 24 in the basket 12 and the opening 20.

A level indicator 25, according to the invention, is mounted on a bracket 26 suitably fixed to the cover 18 adjacent one end of the chute 19. The full indicator 25 is shown in FIG. 3 to include a suitable power source, such as battery 28, an emitter 30, a detector 32 and an alarm or indicator 34. The emitter 30 and the detector 32 are connected to the power source 28 for being energized through an on/off switch 36. The emitter 30 may be any light source, but preferably is a light emitting diode (LED) which emits light in the infra red frequency range. The detector 32 is any well known device responsive to the light spectrum for providing a signal to the alarm 34. The use of an infra red emitter and detector minimizes the possibility that ambient light will activate the detector 32.

Any conventional alarm or signalling device may be employed. In the illustrated embodiment, the alarm 34 includes an actuator 37 responsive to a signal from the detector 32 for actuating an indicator, symbolized by a lamp 40. The lamp 40 may be a red LED which the actuator 37 may energize upon the receipt of a signal from detector 32 or alternately the actuator 37 may energize the lamp 40 when the signal from the detector 32 is interrupted.

The level indicator 25 may also include reflector means for projecting the beam from the emitter 30 across the container at the maximum desired level for sharps 24. In the preferred embodiment, the reflector means comprises a pair of reflectors or mirrors 42 and 44 positioned in an opposed relation on the inner surfaces of the end walls 15 and 16 of basket 12. The reflectors 42 and 44 are positioned at an elevation corresponding to the upper limit desired for the sharps 24 contained within the basket 12. Reflector 42 is oriented substantially vertically and reflector 44 is positioned at an angle θ from the vertical so that it will receive incident infrared light along path A from the emitter 30 and redirect the light generally horizontally along path B to reflector 42 which, in turn, reflects the light backwardly along the path C where it is redirected by reflector 44 along path D to the detector 32. The mirrors 42 and 44 are oriented such that the paths C and D are slightly offset from paths A and B, respectively.

In the illustrated embodiment, the reflectors 42 and 44 are flat so that the angle of reflection is equal to the angle of incidence. However, it will be appreciated that reflectors having ground or curvex reflectors may also be employed for focusing or spreading the beam as desired.

In the illustrated embodiment, the angle θ is the combination of a draft angle of the side 15 of the basket 12 and the angle β between the surface of the side 15 and the reflector 44. The draft angle of one well-known SDC container is about 1.5°. Assuming, for example, a container width of about 10.5 inches and a depth of about 2.5 inches between the cover 18 and the path B, the angle θ would about 6.7° so that the angle β between the side wall 15 and the reflector 44 would be about 5.2° for an SDC having the dimensions indicated.

A line perpendicular to the surface of the reflector 44 forms an angle θ with the horizontally projected paths B and C. Accordingly, if a flat reflector is employed, in order for the beam to be reflected along the path B, it is necessary to orient the level indicator 25 so that the path A of the beam from emitter 30 forms an angle of two 2 θ.

The foregoing is intended as an example only, it being appreciated that the various angles are dependant upon the relative positions and orientations of the various components and the nature of the reflectors.

FIG. 4 shows an alternate embodiment of the invention wherein a counter 48 is connected to the actuator 36. Each time a sharp 24 cuts the beams B or C, which interrupts the beam D to the detector 32, the actuator receives a signal which is counted by the counter 48. This allows the medical staff to inventory the sharps which are disposed within the SDC container 10. When the beam D is interrupted permanently as a result of sharps accumulating in the container 10 to the desired level, the alarm or indicator 40 is actuated.

FIG. 5 shows an alternate embodiment of the invention wherein the emitter 30 and detector 42 are oriented generally vertically downwardly and the reflector 44 is oriented at about 45° relative to vertical. The downwardly directed beam E is reflected horizontally along path F and returned horizontally along path G and upwardly along path H to the detector 32.

In the embodiment of FIG. 6, the emitter 30 is positioned to project the beam along path J toward the reflector 44 which redirects the beam generally horizontally across the container 12 along path K. Reflector 42 is oriented at about 45° relative to the vertical for projecting the beam along path L upwardly toward the detector 32 which is oriented generally vertically downward. Of course, the positions and orientations of the emitter 30 and the detector 32 can be reversed so that the beam is projected vertically downwardly from the emitter 30, is projected across the basket 12 and then upwardly at an oblique angle to the detector 32.

In another embodiment of the invention as shown in FIG. 7 the emitter 30 is oriented for projecting the beam along path M through a window 48 in the end wall 16 of basket 12 to the generally vertical oriented mirror 42 which reflects backwardly along the path N to the detector 32 positioned behind the window 48.

In the embodiment of FIG. 8, the emitter 30 is located adjacent one window 52 in one side wall 16 of container 12 and the detector 32 is adjacent a second window 54 in the opposite side with the beam of infra red radiation travelling along the path P.

In another embodiment shown in FIG. 9, the emitter 30 and detector 32 are mounted above the container 12 and on its opposite sides. The reflectors 42 and 44 are both oriented at 45° relative to the vertical and the emitter 32 and detector are oriented vertically downwardly. The infra red beam follows the path R, S and T from emitter to detector.

The embodiments of FIGS. 5–9 illustrate that the emitter 30 and detector 32 can have various orientations and positions so long as the infrared or other light beam passes generally horizontally across the basket 12 at the desired level.

In a further embodiment illustrated in FIG. 10, the emitter 30 is positioned above the basket 12 for projecting the beam along the path U to the reflector 42 which redirects the beam along the path V through window 54 to the detector 32.

Figure 11:
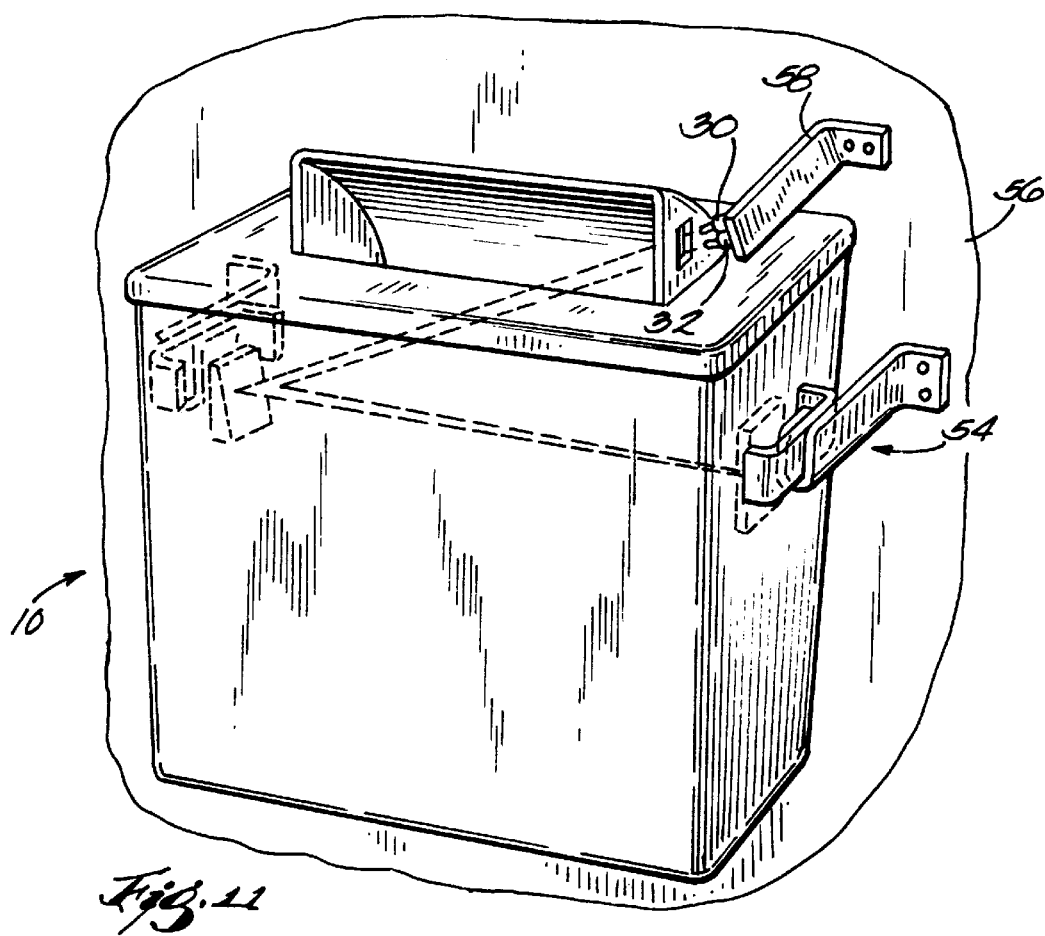

In the embodiment of FIG. 11, the container 10 is suspended by brackets 54 extending from a mobile cart or wall 56. The emitter 30 and the collector 32 are also mounted on the cart or wall 56 by any suitable means, such as, by brackets 58. In this manner, the container 10 can be removed and replaced when full while the emitter 30 and detector remain in place.

While only a few embodiments of the invention has been illustrated and described, it is not intended to be limited thereby but only by the scope of the appended claims. For example, instead of a beam in the light frequency range, radiation in the ultra sonic range may be employed using a suitable emitter, means for projecting the beam across the container at the desired maximum level and means for detecting when the beam is interrupted.

We claim:

1. A sharps disposal container comprising a container having an interior and including a cover, an opening formed in the cover to permit sharps to be inserted into the interior of the container, an emitter and a detector mounted adjacent to the container, said emitter being oriented for projecting a beam toward the container, means mounted on the container for redirecting the beam across the container at a predetermined level and for redirecting the beam to the detector, an indicator coupled to the detector, said detector being operative to actuate said indicator when the level of sharps in the container reaches the predetermined level to interrupt the beam.

2. The sharps disposal container set forth in claim 1 wherein said container has a first side and an opposite side, the emitter and detector being positioned above the cover and adjacent the one side of the container, said emitter being oriented to project a beam toward the opposite side of the container, the means for redirecting the beam comprising a first reflector on the opposite side of the container for receiving the beam from the emitter and being oriented to reflect the beam across the container at the predetermined level and toward the first side of the container, a second reflector mounted on the first side of the container and positioned and oriented for receiving the beam and for redirecting the beam whereby the beam is reflected to the detector.

3. The sharps disposal container set forth in claim 2 wherein said second reflector is oriented for reflecting the beam back across the container and to the first reflector, the first reflector is oriented for projecting the beam to the detector.

4. The sharps disposal container set forth in claim 1 wherein said reflector means includes a pair of spaced apart reflectors mounted in the container and oriented for receiving the beam from the emitter and for projecting the beam across the container at the predetermined level and for redirecting the beam to the detector.

5. The sharps disposal container set forth in claim 1 and including a counter coupled to the detector for receiving a signal each time an object interrupts the beam, said counter being operative to indicate the total number of interruptions so that the number of sharps deposited in the container can be determined.

6. A sharps disposal container comprising a container having an interior and including a cover, an opening in the cover to permit sharps to be inserted into the interior of the container, an emitter and a detector mounted adjacent to the container, said emitter being oriented for projecting a beam toward the container, means disposed within the container for directing the beam across the container at a predetermined level and for redirecting the beam to the detector, an indicator coupled to the detector, said detector being operative to actuate said indicator when the level of sharps in the container reaches the predetermined level to interrupt the beam.

7. The sharps disposal container set forth in claim 6 wherein the emitter and detector are positioned above the cover, said emitter being oriented to project a beam toward the interior of the container, the redirecting means comprising a first reflector disposed within the container for receiving the beam from the emitter and being oriented to reflect the beamm across the container at the predetermined level, said redirecting means also including a second reflector mounted within the container for redirecting the beam whereby the beam is reflected to the detector.

8. The sharps disposal container set forth in claim 7 wherein said second reflector is oriented for reflecting the beam back across the container and to the first reflector, the first reflector being oriented for projecting the beam to the detector.

9. The sharps disposal container set forth in claim 6 wherein said redirecting means include a pair of spaced apart reflectors mounted in the container and oriented for receiving the beam from the emitter and for projecting the beam across the container at the predetermined level and for redirecting the beam to the detector.

10. The sharps disposal container set forth in claim 9 wherein the container has a first side and an opposite side, said pair of reflectors comprising a first reflector positioned on the first side of the container and the second reflector on the opposite side of the container, the emitter being oriented to project at beam to the first reflector, the first reflector being oriented to project the beam to the second reflector, said second reflector being oriented to redirect the beam so that the beam is projected to the detector.

11. The sharps disposal container set forth in claim 10 wherein said second reflector is oriented for reflecting the beam back across the container and to the first reflector, the first reflector being oriented for projecting the beam to the detector.

12. The sharps disposal container set forth in claim 6 wherein said emitter and detector are mounted on the container.

13. The sharps disposal container set forth in claim 6 and including container support means for supporting said container, said emitter and detector being mounted on said container support means adjacent to and separate from the container.

14. The sharps container set forth in claim 13 wherein said container support means is a wall.

15. The sharps container set forth in claim 13 wherein said container support means is a cart.

16. A sharps disposal container comprising a container, an opening in the container for receiving sharps, means for projecting a beam across the container at the maximum desired level of sharps in the container, and means for detecting the passage of the beam across the container and for providing a signal when the beam is interrupted by the presence of sharps in the path of the beam.

\* \* \* \* \*